United States Patent [19]
Lovejoy et al.

[11] Patent Number: 5,429,129
[45] Date of Patent: Jul. 4, 1995

[54] APPARATUS FOR DETERMINING SPECTRAL ABSORPTION BY A SPECIFIC SUBSTANCE IN A FLUID

[75] Inventors: David A. Lovejoy; Robert L. Young, both of Waukesha, Wis.; Bert D. Heinzelman, Tenafly, N.J.

[73] Assignee: Sensor Devices, Inc., Waukesha, Wis.

[21] Appl. No.: 149,011

[22] Filed: Nov. 8, 1993

Related U.S. Application Data

[63] Continuation of Ser. No. 748,637, Aug. 22, 1991, abandoned.

[51] Int. Cl.$^6$ ............................................. A61B 5/00
[52] U.S. Cl. ................................................ 128/633
[58] Field of Search ................... 128/633–634, 128/637, 664–667; 356/39–41

[56] References Cited

U.S. PATENT DOCUMENTS

| | | | |
|---|---|---|---|
| 3,463,142 | 8/1969 | Hart | 128/633 |
| 4,167,331 | 9/1979 | Nielsen | 128/633 |
| 4,446,715 | 5/1984 | Bailey | 128/736 |
| 4,714,080 | 12/1987 | Edgar, Jr. et al. | 128/633 |
| 4,852,025 | 7/1989 | Herpichböhm | 128/633 |
| 4,868,476 | 9/1989 | Respaut | 218/632 |
| 4,890,619 | 1/1990 | Hatschek | 128/24 AA |
| 4,893,284 | 1/1990 | Magrane | 367/12 |
| 4,948,248 | 8/1990 | Lehman | 128/633 |
| 4,968,137 | 11/1990 | Yount | 128/633 |
| 4,974,591 | 12/1990 | Awazu et al. | 128/633 |
| 5,086,229 | 2/1992 | Rosenthal et al. | 128/633 |
| 5,107,847 | 4/1992 | Knute et al. | 128/675 |
| 5,119,831 | 6/1992 | Robin et al. | 128/774 |
| 5,131,391 | 7/1992 | Sakai et al. | 128/633 |
| 5,179,951 | 1/1993 | Knudson | 128/633 |

FOREIGN PATENT DOCUMENTS

| | | |
|---|---|---|
| 0104772 | 4/1984 | European Pat. Off. . |
| 0354736 | 2/1990 | European Pat. Off. . |
| 3809084 | 10/1992 | Germany ......... 128/633 |

*Primary Examiner*—Angela D. Sykes
*Attorney, Agent, or Firm*—Foley & Lardner

[57] ABSTRACT

An apparatus for determining spectral absorption by a specific substance in a fluid having an energy source, a sensor an interface device, a support structure and a connector. The energy source directs energy having a predetermined wavelength into the fluid. The sensor produces an electrical output reflecting the energy it senses and indicative of the spectral absorption of the energy by the specific substance. The interface means generates a reference voltage to allow the apparatus to cooperate with prior art devices. A support means secures the other elements in proximity to the fluid. The connector communicates electrical signals to a remote display device.

29 Claims, 3 Drawing Sheets

APPARATUS FOR DETERMINING SPECTRAL ABSORPTION BY A SPECIFIC SUBSTANCE IN A FLUID

RELATED APPLICATION

This is a continuation of U.S. application Ser. No. 748,637, filed Aug. 22, 1991 for APPARATUS FOR DETERMINING SPECTRAL ABSORPTION BY A SPECIFIC SUBSTANCE IN A FLUID, now abandoned.

BACKGROUND OF THE INVENTION

The present invention is generally directed to an apparatus for determining spectral absorption by a particular substance in a fluid. Specifically, the present invention is directed to a probe apparatus for sensing arterial pulse and blood oxygen saturation in a patient.

A system is needed for non-invasively monitoring pulse and arterial blood oxygen saturation in a patient. Along with blood pressure, pulse rate and blood oxygen saturation are routinely monitored in a patient undergoing surgery or receiving emergency medical treatment. Blood pressure and pulse rate provide essential information about the functioning of the patient's cardiovascular system. Blood oxygen saturation provides information about the patient's ventilation; thus, blood oxygen saturation is a key indicator of the patient's health, whether the patient is human or another animal.

The chemical composition of blood, including oxygen saturation, can be determined by drawing blood samples and employing well-known chemical analysis techniques. However, a non-invasive technique, in which no blood is drawn, is preferred, since drawing blood from a patient adds additional trauma to the patient. Also, analysis of the blood can be an expensive and time consuming procedure and may require elaborate chemical analysis equipment. Such time and equipment may not be readily available, particularly in the context of a medical emergency at a site remote from a hospital or other health care facility. A better technique uses a non-invasive probe which may be disposed after one or a few uses and is simple and inexpensive to manufacture and use. Using such a non-invasive probe yields routinely required information, such as pulse and blood oxygen saturation, by a simple, routine and portable measurement technique.

One method for non-invasively measuring the blood oxygen content of a patient involves monitoring the color of the blood, as disclosed in U.S. Pat. No. 2,414,747 to Kirschbaum for "Method and Apparatus For Controlling the Oxygen Content of the Blood of Living Animals." However, Kirschbaum's sensing apparatus is linked to an additional oxygen administering apparatus which limits its portability. Kirschbaum makes no provision for a disposable probe. Additionally, Kirschbaum's probe must be recalibrated for each use to account for differences in each patient and differences in the lamps used in the probe.

Use of red and infrared light sources in an oximeter is disclosed in U.S. Pat. No. 2,640,389 to Liston for "Oximeter." Liston's light sources are gas tubes containing neon and argon which emit light when excited electrically. Such tubes limit the portability and ruggedness of Liston's system. Also, Liston's probe is not practically disposable since the tubes are relatively expensive to produce.

A similar technique using red and infrared light in an oximeter is disclosed in U.S. Pat. No. 3,412,729 to Smith for "Method and Apparatus for Continuously Monitoring Blood Oxygenation, Blood Pressure, Pulse Rate and the Pressure Pulse Curve Utilizing an Ear Oximeter as Transducer." Smith also uses the data derived from the probe to provide blood pressure information. The oximeter of Smith uses a light bulb as a source of red and infrared energy. Use of an expensive, fragile element such as a light bulb limits the ruggedness and disposability of the Smith device and renders it unsuitable, for example, for emergency medical treatment at remote locations.

Infrared light has also been used to measure the concentration of blood analytes. As disclosed in U.S. Pat. No. 4,882,492 to Schlager for "Non-invasive Near-infrared Measurement or of Blood Analyte Concentrations," near-infrared light having a wavelength greater than 1800 nanometers (nm) is directed into a body part of a patient and sensed to determine the concentration of analytes such as glucose in the blood. As is well known in the art, however, determination of oxygen saturation is preferably achieved using both red and infrared light energy at wavelengths less than 1000 nm.

The probes of Kirschbaum, Liston, Smith and Schlager are preferably attached to the ear of a patient. U.S. Pat. No. 4,865,038 to Rich et al. for "Sensor Appliance for Non-invasive Monitoring" discloses a flexible probe which may be removably attached to a finger or other appendage. Such a probe has the advantages of providing the ability to conform to the appendage while maintaining secure attachment thereto. For medical procedures involving the head and neck, the ear probe could be inconvenient and create interference with access to the head and neck. The ability to attach the probe to a finger, toe or other appendage provides added flexibility and convenience, allowing the probe to be kept from interfering with other procedures. U.S. Pat. No. 4,825,872 to Tan et al. for "Finger Sensor for Pulse Oximetry System" discloses a similar probe which is retained on the finger by means of expansive side panels which expand and contract appropriately to engage the finger.

Rich et al. also disclose the use of solid state devices to generate the red and infrared light energy directed into the patient's blood, and solid state optical sensors to detect light not absorbed by the blood. Specifically, semiconductor light emitting diodes (LEDs) are used because they provide such advantages as small size, ruggedness, ready interface with other solid state circuitry used in the oximeter, long life, and an output having a wavelength that is stable over time.

As is well known in the art, the transmission of light having a wavelength of approximately 660 nm (i.e., red light) through blood is strongly affected by the amount of oxygenated hemoglobin present in the blood. As also known in the art, the transmission of light having a wavelength of approximately 940 nm (i.e., infrared light) is not substantially affected by the amount of oxygenated hemoglobin present. By using these phenomena and shining red light and infrared light through the flesh of a patient, the percent saturation of oxygenation in the patient's blood can be determined.

An oximeter according to the present invention determines blood oxygen saturation based on the intensity of light received by an optical sensor and the known wavelength of an LED. The wavelength of the absorbed light defines an extinction coefficient which the oximeter uses in calculating blood oxygen concentration in a manner known in the art. Consequently, the oximeter must be calibrated to the wavelength of the LEDs employed in the probe. However, different wavelengths of LED light require coefficients having different values be employed for determining blood oxygen concentration. That is, if a probe with a first LED having a first wavelength is replaced by a probe with a second LED having a different second wavelength, the oximeter must use a different coefficient in calculating blood oxygen saturation. An oximeter using such a probe must be recalibrated, therefore, whenever a probe is changed, in order to maintain consistency of measurement and accuracy of results.

U.S. Pat. No. 4,700,708 to New for "Calibrated Optical Oximeter Probe" addressed the need to recalibrate an oximeter when disposable probes are used. New discloses the technique of including in the probe a resistor as an encoding means; the value of the resistor corresponds in a predetermined manner to the wavelengths of the red and infrared LEDs used in the probe. When the probe is manufactured, the LEDs are tested to determine their wavelengths and the appropriate encoding resistor is chosen according to a table. When the probe is connected to the oximeter, a constant current source contained in the oximeter passes current through the resistor thereby enabling the oximeter to read the resistor's value. The New oximeter then uses a corresponding look up table located in semiconductor memory in the oximeter to determine the appropriate wavelength of the LEDs in the probe and to select the requisite extinction coefficients. By using inexpensive components such as LEDs and a resistor, and by eliminating the need to recalibrate the oximeter when the probe is replaced, New provides a truly disposable probe.

The LEDs described by New are selected from batches having only generally known characteristics. Specifically, the wavelength tolerance of the LEDs is large relative to the range permitted by the oximeter. For example, the manufacturing tolerance of the LEDs might be ±20 nm. That is, a LED specified by the manufacturer as having a wavelength of 660 nm actually has a wavelength somewhere in the range from 640 nm to 680 nm. To correctly determine the appropriate extinction coefficients and thereby yield correct measurements, the oximeter must effect calculations based on the actual LED wavelengths within a tolerance of less than 5 nm. Consequently, the use of the resistor to encode the wavelength value is a necessary step in providing a disposable probe. Without the resistor present to encode the LED wavelengths, the New oximeter does not function. To minimize the manufacturing cost of the oximeter probe, New provided for the use of low cost LEDs with a large manufacturing tolerance and a resistor to encode the exact values of the LED wavelengths within their tolerance ranges.

Many present oximeter systems typically do not rely on encoding the LED wavelength values. Manufacturing techniques for LEDs have improved so that LEDs having a tight tolerance—as low as ±2 nm—are inexpensively available. Consequently, the encoding and look up table disclosed in New are not required in competing oximeter systems. Competing systems specify a center value for the LED wavelengths, as for example, 660 nm and 940 nm, and each conforming probe is then supplied with LEDs having those wavelengths.

In addition, the oximeter probe disclosed by New has several shortcomings. To keep manufacturing cost low, the encoding resistor has a large tolerance and a large temperature coefficient of resistance. At extremes of temperature, the encoding resistor will vary considerably from its nominal value, creating the possibility that incorrect extinction coefficients will be read from the look up table by the oximeter. Oximeter systems are used not only in the controlled environments of operating rooms but, also, in the emergency medical treatment context, in situations of environmental temperature extremes. Consequently, the operating temperature of such a system may range from well below zero degrees Fahrenheit to well over one hundred degrees Fahrenheit. Under such extremes, a more precise means of interfacing the probe to the oximeter is needed.

Also, the probe disclosed by New is subject to noise which may cause incorrect readings. Low frequency noise may be misinterpreted by the oximeter to be pulsatile information. Such noise may have its source in radio frequency radiation propagated through the environment, as from other nearby test equipment, or as a motion artifact, due to movement of the bodily appendage to which the probe is attached.

A probe which avoids the encoding technique disclosed by New also provides manufacturing economies. The use of tight-tolerance LEDs eliminates the need to maintain multiple stocks of different wavelength LEDs. A single bin of devices can be used, reducing storage costs. The necessary step of testing LED wavelengths is eliminated. In addition, the step of matching a resistor to the LED wavelength is eliminated. Using precision LEDs and eliminating the encoding resistor greatly reduces manufacturing cost and complexity.

Accordingly, there is a need for an oximeter probe which can accurately interface with multiple types of oximeter systems, including those which use an encoding resistor and those which specify a center wavelength value, as well as providing precise measurement characteristics in extreme as well as nominal environments, has reduced sensitivity to noise interference, and which is inexpensive enough to manufacture so as to be economically disposable after one or a few uses.

SUMMARY OF THE INVENTION

The present invention provides an apparatus for determining spectral absorption by a specific substance in a fluid and indicating the spectral absorption to a remote display device. The apparatus of the present invention comprises an energy source which emits energy having one or more characteristic wavelengths; a sensing device for sensing the energy emitted by the energy source and producing an electrical output which represents the spectral absorption of the energy by the substance; an interface device which generates a reference voltage which reference voltage interacts with the remote display device; a support structure for supporting the other elements in proximity to the fluid; and a connector for communicating the electrical output to the remote display device.

In its preferred embodiment, the energy source comprises at least one light emitting diode. Preferably, the energy source emits both red light and infrared light. Also, in its preferred embodiment, the interface means comprises a voltage regulator.

The present invention further provides a pulse oximeter probe for non-invasively determining vascular oxygen saturation and pulse frequency in a patient. The pulse oximeter probe of the present invention comprises one or more light emitting diodes which direct light having a predetermined wavelength into tissue of the patient; a sensor which senses the light directed by the light emitting diodes and produces an electrical signal which reflects the amount of energy sensed; a voltage source which generates a substantially constant output voltage, which voltage reflects the predetermined wavelength of the light emitting diodes; and an assembly structure which supports the other elements adjacent the tissue of the patient.

In its preferred embodiment, the light emitting diodes of the pulse oximeter probe of the present invention emit light having wavelengths corresponding to red and infrared light. The voltage source is preferably independent of variations in supply voltage and temperature. In addition, the pulse oximeter preferably includes a connector for communicating the electrical signal from the sensor and the output voltage from the voltage source to a remote display device.

The present invention still further provides a pulse oximeter probe for non-invasively sensing the arterial pulse frequency and percent oxygen saturation of the blood of a living patient and communicating with a display device. The pulse oximeter probe of the present invention comprises one or more light emitting diodes, which are responsive to the display device, which direct light energy into the tissue of the patient, the light energy being partly absorbed by the blood of the patient according to a known extinction coefficient corresponding to the predetermined wavelength and being partly reflected by the blood; a sensor which senses the intensity of light energy from the light emitting diodes and not absorbed by the blood and converts the intensity of the light energy to an electrical signal; a precision voltage regulator means which generates a voltage reflecting the predetermined wavelength and the extinction coefficient, which voltage is substantially independent of variations in temperature or supply voltage and electrical noise, and which voltage cooperates interactively with the display device; a support structure for detachably supporting the one or more light emitting diodes, the sensor, and the precision voltage regulator adjacent the tissue of the patient; and a connector which communicates the electrical signal and the voltage to the display device.

In its preferred embodiment, the support structure of the pulse oximeter probe of the present invention comprises a structure for attaching the probe to the patient's finger. Preferably, the light emitting diodes are responsive to a control signal from the display device, which control signal is preferably communicated from the display device to the light emitting diodes by means of the connector.

Further objects and features of the present invention will be apparent from the following specification and claims when considered in connection with the accompanying drawings illustrating the preferred embodiment of the present invention.

DETAILED DESCRIPTION OF THE DRAWINGS

DETAILED DESCRIPTION OF THE INVENTION

Figure 1:
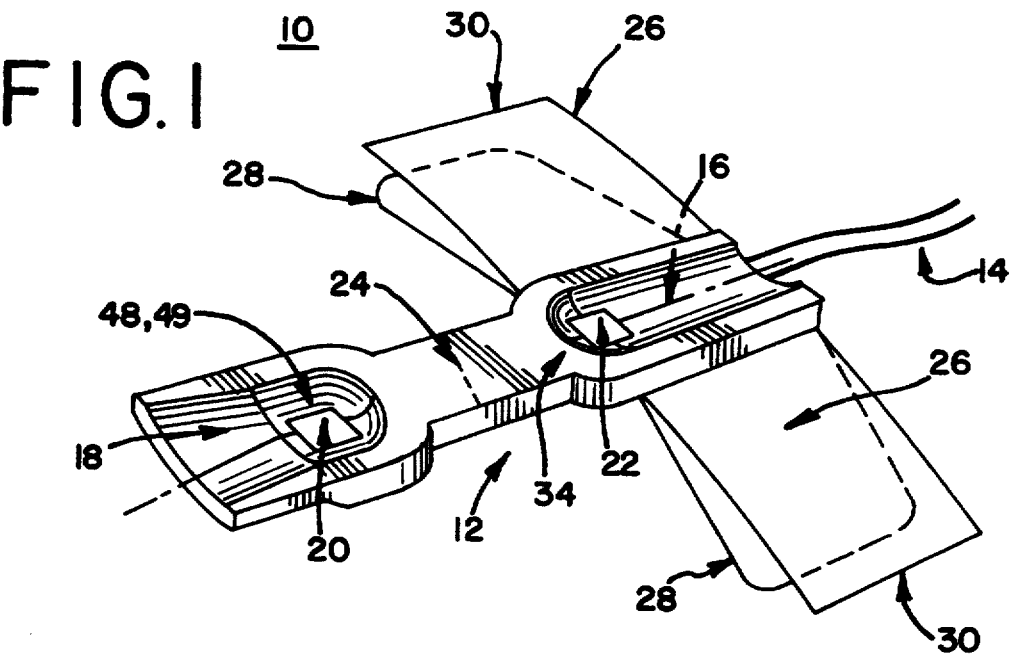
FIG. 1 is a perspective view of a pulse oximeter probe employing the preferred embodiment of the present invention.

FIG. 1 is a perspective view of a pulse oximeter probe employing the preferred embodiment of the present invention. In FIG. 1, pulse oximeter probe 10 includes assembly 12 and connector 14. Connector 14 provides electrical connection to the remote pulse oximeter, not shown, as well as mechanical support and strain relief for assembly 12.

Assembly 12 includes first finger locator 16 and second finger locator 18. Finger locators 16 and 18 are depressions formed in assembly 12 which allow probe 10 to grippingly engage a patient's finger. Probe 10 may also engage the patient's toe or other bodily appendage. Assembly 12 is preferably formed of a flexible material which is impervious to dirt and grease and which may be readily wiped clean with water or alcohol, such as Alcryn, sold by DuPont Corp.

In FIG. 1, assembly 12 is shown in its stored, unflexed position. In use, assembly 12 preferably flexes along centerline 24. In this manner, first finger locator 16 engages the lower surface of the patient's finger and second finger locator 18 engages the upper surface of the patient's finger. Attached to assembly 12 are tie down tabs 28. The underside of tie down tabs 28 is coated with an adhesive material 30. When probe 10 is not in use, adhesive material 30 is protectively covered by paper strips 26. Paper strips 26 prevent dirt and other contaminants from contacting adhesive material 30. When probe 10 is placed on a patient's finger, assembly 12 is flexed along centerline 24 allowing finger locators 16, 18 to engage the patient's finger. Paper strips 26 are removed, exposing adhesive material 30. Tie down tabs 28 are then folded up so as to secure assembly 12 in place on the patient's finger. Tie down tabs 28 attach to assembly 12 and to one another by means of adhesive material 30. Preferably, probe 10 is held firmly in place on the patient's finger so as to ensure a fit which does not impede blood circulation in the patient's finger. Use of adhesive material 30 allows probe 10 to be reused multiple times on one or more patients before being discarded.

Assembly 12 includes LED mount 20 and sensor mount 22. One or more light emitting diodes 32 are mounted in LED mount 20. Preferably, two light emitting diodes 32, one having a wavelength corresponding to red light and one having a wavelength corresponding to infrared light, are mounted in LED mount 20. An optical sensor 34, sensitive to the wavelengths of light emitted by light emitting diodes 32 mounted in LED mount 20, is mounted in sensor mount 22. Optical sensor 34 preferably converts the intensity of light striking optical sensor 34 into an electrical signal, such as an electrical current.

In operation, probe 10 is fitted to a patient's finger. Light emitting diodes 48, 49 respond to signals communicated by connector 14 from a remote pulse oximeter. Light emitting diodes 48, 49 direct light of a predetermined wavelength into the patient's finger. For example, light emitting diodes 48, 49 might direct red light having a wavelength of 660 nm and infrared light having a wavelength of 940 nm into the patient's finger. As is well known in the art, some of the light is absorbed by the oxygenated hemoglobin in the patient's blood. Some of the light is reflected and diffused through the patient's finger and strikes optical sensor 34. Optical sensor 34 produces an electrical signal reflecting the intensity of the light striking optical sensor 34. The electrical signal is communicated by means of connector 14 to the remote pulse oximeter which determines the percent oxygen saturation of the patient's blood and produces an appropriate display.

Figure 2:
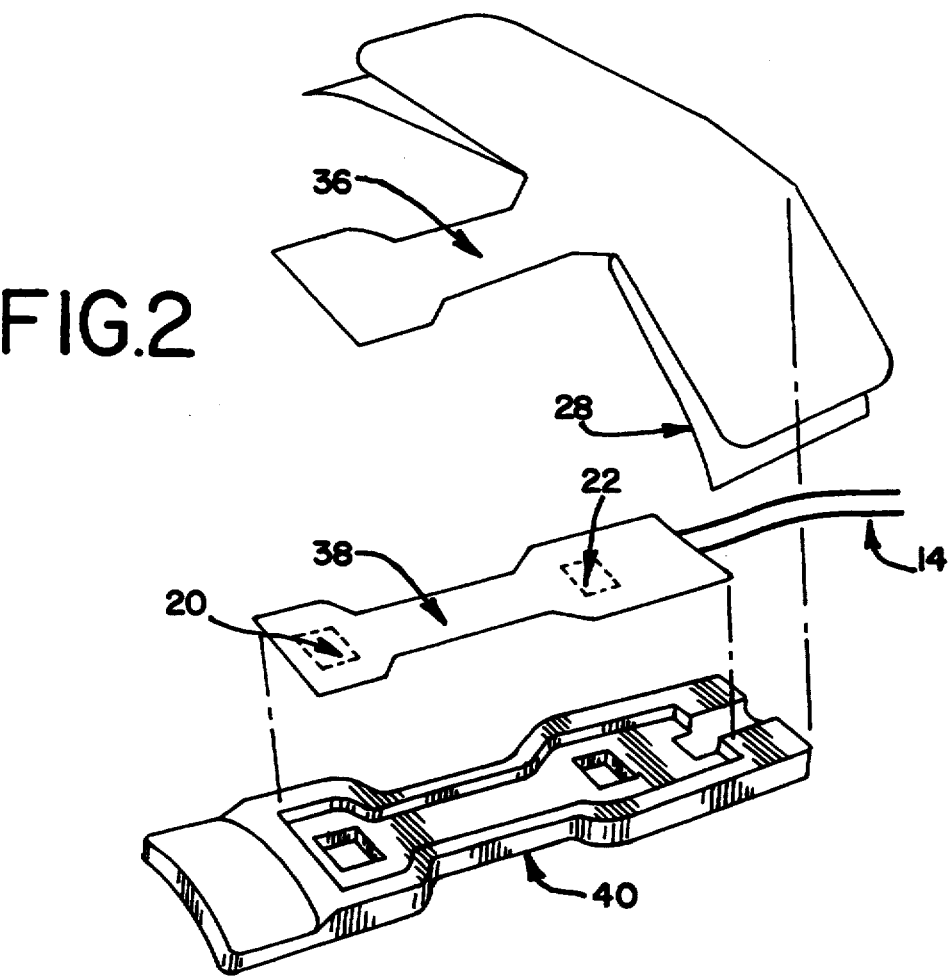
FIG. 2 is an exploded perspective view of a pulse oximeter probe employing the preferred embodiment of the present invention.

FIG. 2 is an exploded perspective view of a pulse oximeter probe employing the preferred embodiment of the present invention. In FIG. 2, chassis 40 forms the base for probe 10. Chassis 40 is preferably molded from a flexible material, such as Alcryn. Printed circuit board 38 is mounted on chassis 40. Printed circuit board 38 is preferably formed of a flexible material such as mylar. Connector 14 is attached to printed circuit board 38. Connector 14 is attached both electrically and mechanically to circuit board 38. Flexible laminate 36 is attached to chassis 40 so as to completely enclose printed circuit board 38. Printed circuit board 38 is thereby protected from contamination.

Figure 3:
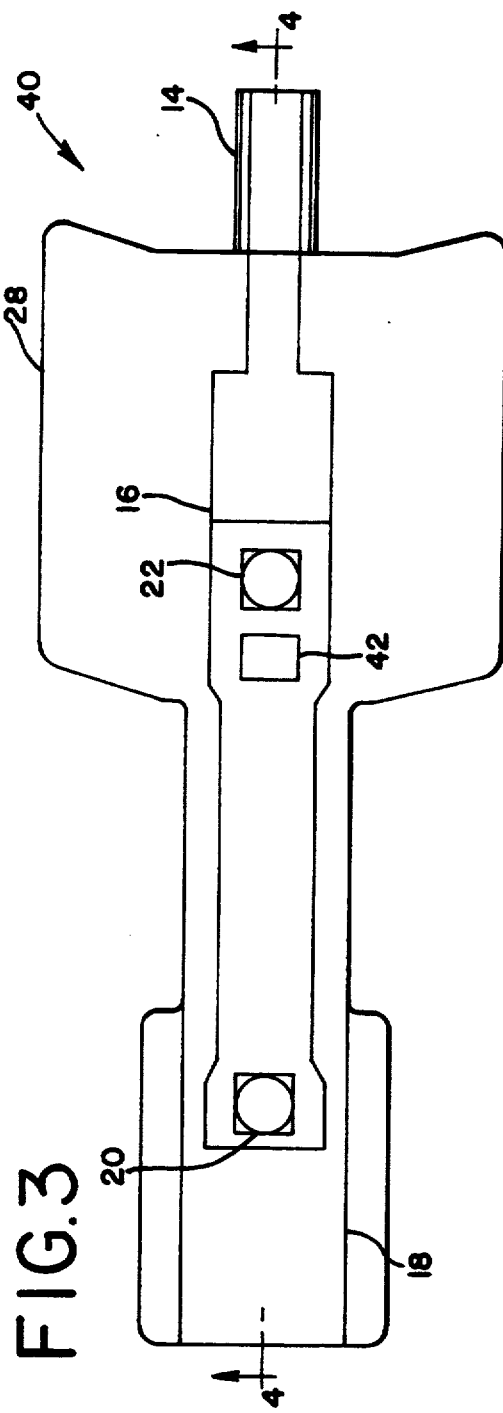
FIG. 3 is a top view of the chassis of a pulse oximeter probe employing the present invention.

FIG. 3 is a top view of chassis 40. FIG. 3 shows light emitting diode mount 20 in line with sensor mount 22 and voltage source mount 42. Light emitting diode mount 20 and sensor mount 22 preferably comprise perforations in chassis 40. Voltage source mount 42 preferably comprises a depression in chassis 40. These provide mechanical clearance for the active circuit components mounted on printed circuit board 38.

Figure 4:
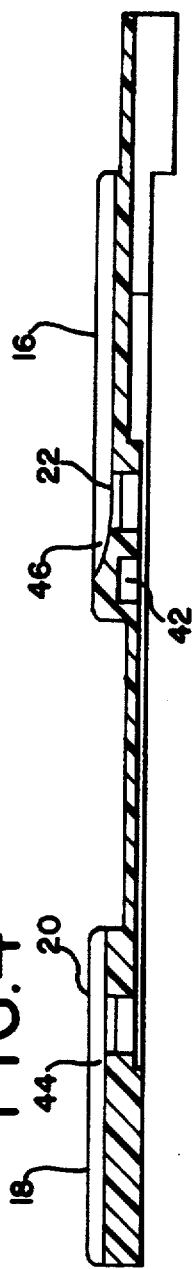
FIG. 4 is a side view of the chassis of FIG. 3 taken at section AA of FIG. 3.

FIG. 4 is a side view of chassis 40 in partial section taken at section AA of FIG. 3. FIG. 4 shows curved faces 44, 46 in the upper surface of chassis 40. Curved face 44 is located at first finger locator 16. Curved face 46 is located at second finger locator 18. When probe 10 is in place on a patient's finger, curved faces 44, 46 engage the surface and edges of the finger to prevent lateral slippage.

Figure 5:
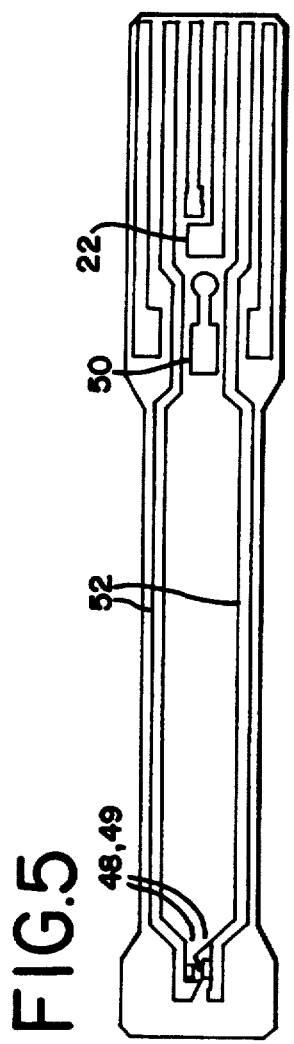
FIG. 5 is a top view of the printed circuit board of a pulse oximeter probe employing the preferred embodiment of present invention.

FIG. 5 is a top view of printed circuit board 38 of a pulse oximeter probe employing the present invention. FIG. 5 shows preferred dimensions of printed circuit board 38. Traces 52 are located on the surface of printed circuit board 38 and are preferably formed of a flexible or malleable electrical conductor such as copper. When probe 10 is in use, traces 52 are in electrical contact with connector 14, not shown. Traces 52 carry electrical signals, power supply voltages and ground potential between the active components of probe 10 and connector 14. FIG. 5 also shows light emitting diodes 48, 49 mounted on printed circuit board 38. Light emitting diodes 48, 49 are fixedly attached to printed circuit board 38, for example, by eutectic bonding. Preferably, light emitting diodes 48, 49 emit light having a wavelength corresponding to red light and light having a wavelength corresponding infrared light. Also, FIG. 5 shows sensor mount 22 and module mount 50 on printed circuit board 38.

Figure 6:
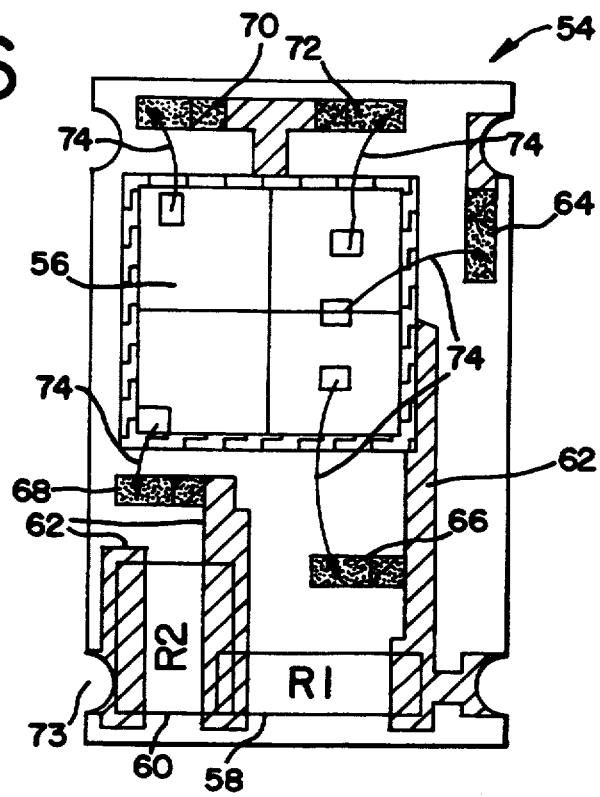
FIG. 6 is a top view of the interface module of a pulse oximeter probe employing the preferred embodiment of the present invention.

FIG. 6 is a top view of interface module 54 of a pulse oximeter probe employing the preferred embodiment of the present invention. Interface module 54 is rigidly attached to printed circuit board 38 at module mount 50, for example, by eutectic bonding. Voltage regulator 56 is mounted on interface module 54. Voltage regulator 56 is preferably configured as an integrated circuit.

Interface module 54 also includes resistor 58 and resistor 60. Resistors 58, 60 are preferably formed from conductive ink printed on the surface of interface module 54. When interface module 54 is assembled and tested, resistors 58, 60 may preferably be trimmed to a precise value. Laser trimming ensures that resistors 58, 60 have a manufacturing tolerance of ±1% Interconnect metal 62 is located on the surface of interface module 54 and connects resistors 58, 60 and voltage regulator 56.

In the embodiment illustrated in FIG. 6, interface module 54 includes IN terminal 64, OUT terminal 66, ADJUST terminal 68, SENSE terminal 70, VOUT terminal 72 and ground connection terminal 73. These terminals 64, 66, 68, 70, 72, 73 connect to printed circuit board 38. Voltage regulator 56 is connected to these terminals 64, 66, 68, 70, 72, 73 by wire bonds 74.

Figure 7:
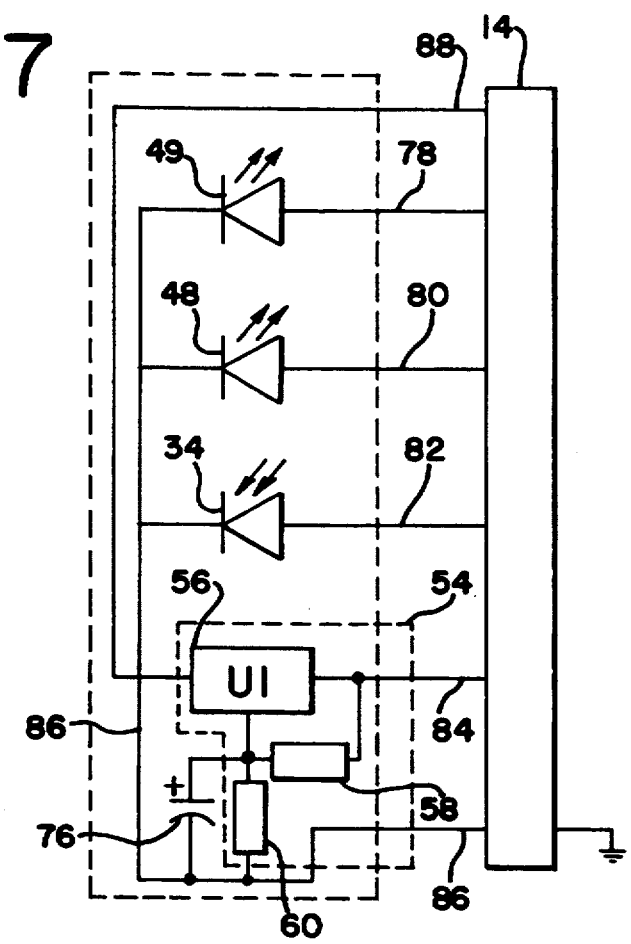
FIG. 7 is a schematic diagram of the circuit of a pulse oximeter probe employing the preferred embodiment of the present invention.

FIG. 7 is a schematic diagram of the circuit of a pulse oximeter probe employing the preferred embodiment of the present invention. In FIG. 7, terminals 78, 80, 82, 84, 86 are coupled to connector 14. FIG. 7 shows light emitting diodes 48, 49, optical sensor 34, voltage regulator 56, resistors 58, 60 and capacitor 76. Light emitting diodes 48, 49 are coupled between terminals 78, 80 and terminal 86. Optical coupler 30 is coupled between terminal 82 and terminal 86. Terminal 88 is preferably coupled to IN terminal 64 of interface module 54 (see FIG. 6). Terminal 84 is preferably coupled to OUT terminal 66 of interface module 54 (FIG. 6). Terminal 86 is preferably coupled to ground connection 73 of interface module 54 (FIG. 6). Terminal 86 is preferably coupled to system ground. In the preferred embodiment illustrated in FIG. 7, terminal 88 is coupled to a system voltage (not shown) preferably in the range of 0 to 5 volts.

Capacitor 76 filters low and high frequency electrical noise from the output voltage generated at terminal 84. Such noise may have its source in radio frequency radiation caused by other nearby test equipment or as a motion artifact, as when probe 10 is attached to a moving patient, such as an infant, causing the probe to move in relation to the patient.

In the preferred embodiment, voltage regulator 56 is a precision adjustable voltage regulator which preferably provides an output voltage at terminal 84 which is substantially invariant with variations in temperature and supply voltage and maintains these characteristics over an operating range from approximately −55° C. to approximately +150° C.

In operation, light emitting diodes 48, 49 receive signals from the remote pulse oximeter (not shown in FIG. 7) by means of connector 14. In response, light emitting diodes 48, 49 direct red and infrared light into the tissue of the patient. A portion of the emitted light is absorbed by the oxygenated hemoglobin in the patient's blood. The balance of the light passes through the tissue and is incident on optical sensor 34. Optical sensor 34 senses the intensity of the incident light and generates an electrical signal representing that intensity. The electrical signal is communicated to the remote pulse oximeter via connector 14.

The remote pulse oximeter receives the electrical signals and calculates percent oxygen saturation in a manner known in the art. The calculation includes use of extinction coefficients which are dependent for their value on the wavelength of the incident light. Many commercially available pulse oximeter systems specify standard values for the wavelength of the light to be emitted by the light emitting diodes contained in conforming probes, for example, a red LED having a wavelength of 660 nm and an infrared LED having a wavelength of 940 nm. The oximeter system then uses extinction coefficients corresponding to the specified LED wavelengths to calculate percent oxygen saturation.

Other pulse oximeter systems do not specify a particular LED wavelength for conforming probes but rather specify a range of wavelengths. The probe must then additionally include an encoding means such as a resistor to communicate to the oximeter system the exact values of wavelength of the LEDs assembled with the probe. The pulse oximeter in such a system includes a constant current source which passes current through the encoding resistor, generating a reference voltage which can be read by the pulse oximeter system. The pulse oximeter system uses the reference voltage to determine, from a look up table located in semiconductor memory, the appropriate extinction coefficient. By using this technique, inexpensive LEDs having a wide tolerance, such as ±20 nm, may be used in the pulse oximeter probe. The encoding resistor specifies the precise value of the LED wavelength within the tolerance range.

The present invention allows pulse oximeter probe 10 to interface with both types of pulse oximeter systems. LEDs with very tight wavelength tolerances, such as ±2 nm, are inexpensively available. For pulse oximeter systems that specify LED wavelengths, light emitting diodes 48, 49 can be chosen when probe 10 is assembled to correspond to the specified values. In applications in which probe 10 is used with such pulse oximeter systems, voltage regulator 56 does not interfere with the system.

In pulse oximeter systems which permit a range of LED wavelengths to be used and require a reference voltage from the probe to identify the wavelength of LEDs employed in the probe, voltage regulator 56 generates the required reference voltage and configures probe 10 to interface with the pulse oximeter system. Thus, voltage regulator 56, with resistors 58, 60, generates a precisely regulated voltage at terminal 84 reflecting the wavelengths of light emitting diodes 48, 49. The pulse oximeter system uses the regulated voltage on terminal 84 to determine the appropriate extinction coefficients.

Use of voltage regulator 56 and resistors 58, 60 provides distinct advantages over prior art designs, such as oximeter probes using an encoding resistor. Except for precision resistors, the cost of which would be prohibitively high for manufacturing a competitively priced oximeter probe which could be economically discarded after one or a few uses, resistors generally exhibit great variation in their value with temperature and offer an inacceptably wide tolerance in their specified value.

A pulse oximeter system may be used in providing emergency medical treatment away from a controlled hospital environment, often at extremes of temperature. In such circumstance, the value of a resistor may vary too greatly to reliably accurately establish a reference voltage for an oximeter, thereby causing the wrong extinction coefficients to be employed by the oximeter so that incorrect conclusions may result from measurements taken.

In contrast to such unreliable operation by a resistor, voltage regulator 56 generates a temperature and voltage compensated reference voltage. Resistors 58, 60 may be laser trimmed during manufacturing ensuring accuracy within one percent of a specified value for a reference voltage. Thus, with the present invention, the proper reference voltage is always presented by the probe to the remote pulse oximeter system, thereby assuring correct values for extinction coefficients are employed by the oximeter system. In addition, capacitor 76 filters electrical noise which may appear as false pulsatile information and cause incorrect readings.

It is to be understood that, while the detailed drawings and specific examples given describe preferred embodiments of the invention, they are for the purpose of illustration only, that the apparatus of the invention is not limited to the precise details and conditions disclosed, and that various changes may be made therein without departing from the spirit of the invention which is defined by the following claims.

I claim:

1. An apparatus for determining spectral absorption by a specific substance in a fluid and indicating said spectral absorption to a remote display device, the apparatus comprising:

an energy source, said energy source emitting energy having one or more predetermined wavelengths, said energy being partly absorbed by said fluid in accordance with a known extinction coefficient corresponding to said one or more predetermined wavelengths;

a sensing means for sensing energy emitted by said energy source, said sensing means producing an electrical output representing said spectral absorption;

an interface means for supplying a predetermined reference voltage representing said one or more predetermined wavelengths and said extinction coefficient, said reference voltage cooperatively interacting with said remote display device;

a support means for supporting said energy source, said sensing means and said interface means in proximity to said fluid; and connector means for communicating said electrical output and said reference voltage to said remote display device.

2. An apparatus for determining spectral absorption as recited in claim 1 wherein said energy source comprises at least one light emitting diode.

3. An apparatus for determining spectral absorption as recited in claim 2 wherein said energy source comprises a first light emitting diode emitting red light and a second light emitting diode emitting infrared light.

4. An apparatus for determining spectral absorption as recited in claim 1 wherein said interface means comprises a voltage regulator.

5. A pulse oximeter probe for non-invasively determining vascular oxygen saturation and pulse frequency in a patient, the pulse oximeter probe comprising:

one or more light emitting diode means for directing light into tissue of said patient, said light having a predetermined wavelength, said light being partly absorbed in accordance with a known extinction coefficient corresponding to said predetermined wavelength;

a sensing means for sensing light directed by said light emitting diode means, said sensing means producing an electrical signal representing the amount of energy sensed;

a voltage source means for supplying a predetermined, substantially constant output voltage, said voltage representing said predetermined wavelength and said extinction coefficient in a predetermined manner; and an assembly means for cooperatively supporting said one or more light emitting diode means, said sensing means, and said voltage source means adjacent said tissue of said patient.

6. A pulse oximeter probe as recited in claim 5 wherein said one or more light emitting diode means directs light having a wavelength corresponding to red light and a wavelength corresponding to infrared light.

7. A pulse oximeter probe as recited in claim 5 wherein said voltage source means comprises a voltage regulator.

8. A pulse oximeter probe as recited in claim 5 wherein said output voltage is substantially independent of variations in supply voltage and temperature.

9. A pulse oximeter probe for non-invasively sensing the arterial pulse frequency and percent oxygen saturation of the blood of a living patient and communicating with a display device, the pulse oximeter probe comprising:

one or more light emitting diode means for directing light energy into the tissue of said patient, said light emitting diode means being responsive to said display device, said light energy having a predetermined wavelength, said light energy being partly absorbed by said blood of said patient in accordance with a known extinction coefficient corresponding to said predetermined wavelength and said light energy being partly reflected by said blood;

a sensing means for sensing intensity of light energy directed by said one or more light emitting diode means and not absorbed by said blood, and converting said intensity of light energy to an electrical signal;

a precision voltage regulator means for supplying a predetermined, substantially constant, voltage representing said predetermined wavelength and said extinction coefficient, said voltage being substantially independent of variations in temperature or supply voltage and electrical noise and said voltage cooperating interactively with said display device;

a support means for detachably supporting said one or more light emitting diode means, said sensing means, and said precision voltage regulator means adjacent said tissue of said patient; and connector means for communicating said electrical signal and said voltage to said display device.

10. A pulse oximeter probe as recited in claim 9 wherein said support means comprises a means for attaching said pulse oximeter probe to a finger of said patient.

11. A pulse oximeter probe for non-invasively sensing the arterial pulse frequency and percent oxygen saturation of the blood of a living patient and communicating with a display device, the pulse oximeter probe comprising:

one or more light emitting diode means responsive to a control signal from said display device for directing light energy into the tissue of said patient, said light energy having a predetermined wavelength, said light energy being partly absorbed by said blood of said patient in accordance with a known extinction coefficient corresponding to said predetermined wavelength and said light energy being partly reflected by said blood;

a sensing means for sensing intensity of light energy directed by said one or more light emitting diode means and not absorbed by said blood, and converting said intensity of light energy to an electrical signal;

a precision voltage regulator means for supplying a predetermined voltage representing said predetermined wavelength and said extinction coefficient, said voltage being substantially independent of variation in temperature or supply voltage and electrical noise and said voltage cooperating interactively with said display device;

a support means for detachably supporting said one or more light emitting diode means, said sensing means, and said precision voltage regulator means adjacent said tissue of said patient; and connector means for communicating said electrical signal and said voltage to said display device.

12. A pulse oximeter probe as recited in claim 11 wherein said connector means further communicates said control signal from said display device to said light emitting diode means.

13. A probe for use with a pulse oximeter, said pulse oximeter producing an indication of arterial pulse rate or percent oxygen saturation of a patient, or both, the probe comprising:

energy means for directing energy into tissue of said patient at one or more predetermined wavelengths;

sensing means for sensing said energy and producing an electrical output representing said percent oxygen saturation;

interface means for supplying a substantially constant reference signal to said pulse oximeter, said reference signal corresponding to said one or more predetermined wavelengths in a predetermined manner, said reference signal cooperatively interacting with said pulse oximeter; and connector means for communicating said electrical output and said reference signal to said pulse oximeter.

14. A probe for use with a pulse oximeter as recited in claim 13 wherein the probe further comprises support means for supporting said energy means, said sensing means and said interface means adjacent said tissue of said patient.

15. A probe for use with a pulse oximeter as recited in claim 14 wherein said support means comprises means for grippingly engaging a finger of said patient.

16. A probe for use with a pulse oximeter as recited in claim 13 wherein said reference signal comprises a voltage.

17. A probe for use with a pulse oximeter as recited in claim 16 wherein said voltage is substantially independent of variations in temperature or supply voltage and electrical noise.

18. A probe for use with a pulse oximeter as recited in claim 17 wherein said interface means comprises a voltage regulator for generating said voltage.

19. A probe for use with a pulse oximeter as recited in claim 13 wherein said energy means comprises at least one light emitting diode.

20. A probe for use with a pulse oximeter as recited in claim 19 wherein said energy means comprises a first light emitting diode directing energy having a first wavelength and a second light emitting diode directing energy having a second wavelength.

21. A probe for use with a pulse oximeter as recited in claim 20 wherein said first wavelength corresponds to red light and said second wavelength corresponds to infrared light.

22. A pulse oximeter probe for use with a pulse oximeter, the pulse oximeter producing an indication of vascular oxygen saturation or pulse frequency or both in a patient responsive to an electrical signal received from said pulse oximeter probe, the pulse oximeter probe comprising:

- an energy source adapted to be coupled with said pulse oximeter, said energy source directing light energy into tissue of the patient, said light energy having at least one predetermined wavelength, said light energy being partly absorbed by said tissue in accordance with at least one extinction coefficient, said at least one extinction coefficient corresponding to said at least one predetermined wavelength, said light energy being partly transmitted through said tissue;
- a photodetector adapted to be coupled with said pulse oximeter, said photodetector sensing said transmitted light energy and producing said electrical signal, said electrical signal representing an amount of light energy sensed; and
- an encoder adapted to be coupled with said pulse oximeter, said encoder supplying a substantially constant encoded signal, said encoded signal encoding said at least one predetermined wavelength, said pulse oximeter decoding said encoded signal to determine said at least one extinction coefficient for producing said indication.

23. A pulse oximeter probe as recited in claim 22 wherein the pulse oximeter probe further comprises a connector for communicating said electrical signal and said encoded signal to said pulse oximeter.

24. A pulse oximeter probe as recited in claim 23 wherein said encoder comprises a voltage source generating a voltage, said voltage having a magnitude corresponding to said at least one predetermined wavelength in accordance with a predetermined relationship.

25. A pulse oximeter probe as recited in claim 24 wherein said voltage source maintains said magnitude substantially constant.

26. A pulse oximeter probe as recited in claim 25 wherein said voltage source comprises a voltage regulator, said voltage regulator establishing said magnitude substantially independent of variations in temperature or supply voltage.

27. A pulse oximeter probe as recited in claim 22 wherein said energy source comprises at least one light emitting diode, each light emitting diode of said at least one light emitting diode emitting light energy at one wavelength of said at least one predetermined wavelength.

28. A pulse oximeter probe as recited in claim 22 wherein the pulse oximeter probe further comprises an assembly, said assembly supporting said energy source, said photodetector and said encoder adjacent said tissue of said patient.

29. A pulse oximeter probe as recited in claim 28 wherein said assembly comprises at least one finger locator for engaging a finger of said patient.

* * * * *